United States Patent [19]
Showell et al.

[11] Patent Number: 5,948,813
[45] Date of Patent: *Sep. 7, 1999

[54] METHOD OF PREVENTING ALLOGRAFT REJECTION

[75] Inventors: Henry J. Showell, Middlesex County, Conn.; Elora J. Weringer, New London County, N.Y.

[73] Assignee: Pfizer Inc., New York, N.Y.

[*] Notice: This patent is subject to a terminal disclaimer.

[21] Appl. No.: 08/949,483

[22] Filed: Oct. 14, 1997

Related U.S. Application Data

[60] Provisional application No. 60/028,878, Oct. 17, 1996.

[51] Int. Cl.$^6$ .................. A61K 31/47; A61K 31/405; A61K 31/40; A61K 31/38
[52] U.S. Cl. .................. 514/456; 514/312; 514/415; 514/417; 514/432; 514/441
[58] Field of Search .................. 514/456, 312, 514/415, 417, 432, 441

[56] References Cited

U.S. PATENT DOCUMENTS

| | | | |
|---|---|---|---|
| 5,550,152 | 8/1996 | Koch et al. | 514/458 |
| 5,552,435 | 9/1996 | Koch | 514/456 |

OTHER PUBLICATIONS

Nilsson et al. European Surgical Research, 17(3) 173–8 [Switzerland](Abstract), 1985.

Szczylik et al. Polskie Archiwum Medycyny Wewnetrznej, 79 (1) 30–7 [Poland] (Abstract), 1988.

*Primary Examiner*—Russell Travers
*Attorney, Agent, or Firm*—Peter C. Richardson; Paul H. Ginsburg; Jolene W. Appleman

[57] ABSTRACT

A method for suppressing the rejection of allogeneic transplants in a mammal, including a human, comprising administering to said mammal an effective amount of the compound of the formula

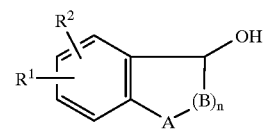

wherein n, A, B, $R^1$ and $R^2$ are as defined above, or the pharmaceutically acceptable salt thereof.

8 Claims, No Drawings

METHOD OF PREVENTING ALLOGRAFT REJECTION

This application includes materials described in provisional application Ser. No. 60/028,878 filed Oct. 17, 1996 and is entitled to the benefits of the filing date thereof.

BACKGROUND OF THE INVENTION

This invention relates to the use of certain benzopyran and benzo-fused compounds and their pharmaceutically acceptable acid addition salts for the prevention of allograft rejection in mammals, including humans.

Allograft rejection, be it of a vascularized organ, skin or tissue, is characterized by a highly complex series of cellular and humoral interactions in which T lymphocytes play a central, essential role. T cells initiate and regulate graft rejection, but a mixed population of cells and effector mechanisms contribute to graft failure. This wide array of effector mechanisms leading to graft destruction include alloantibody dependent mechanisms (B lymphocytes) antigen-specific cytotoxic T cells and a variety of non-specific effector cells including macrophages, natural killer (NK) cells, polymorphonuclear leukocytes (PMN, e.g., neutrophils, eosinophils), and lymphokine- activated killer (LAK) cells. The cellular pathways which mediate graft rejection are multiple and complex.

Acute cellular rejection is the result of migration of inflammatory cells into the graft. Lymphocytes recognize and react to foreign antigens, undergo proliferative expansion and initiate humoral events, i.e., antibodies, cytokines, and proinflammatory mediators; these in turn recruitactivate, non-specifically, various cells of the monocyte/macrophage lineage to infiltrate and destroy graft tissue. Also, at this point, large granular lymphocytes and PMN may be seen in the graft.

Secondarily, most grafts are subject to ischemic injury due to cold ischemia time and vasoconstriction of donor arteries following reperfusion and high dose immunosuppression immediately after transplantation. This event is characterized by infiltration of the graft by inflammatory cells, primarily, monocytes, macrophages and PMN. The donor arterial endothelial cells are most likely the primary target of transplant ischemia-reperfusion injury. This lesion is characterized by a local, chronic cellular immune response of the endothelium composed of T cells and macrophages which continue to amplify and perpetuate the immune/inflammatory response, resulting in loss of intact endothelium and function combined with chronic immunologic injury.

The incidence of transplant associated arteriosclerosis escalates with increasing survival time; lesions develop rapidly (within 3 months) and occur throughout the arterial tree of the graft. Chronic rejection leads to gradual deterorationof graft function and is a major threat to long-term survival of transplanted organs.

SUMMARY OF THE INVENTION

The present invention relates to a method for suppressing the rejection of allogeneic transplants in a mammal, including a human, comprising administering to said mammal an effective amount of a compound of the formula

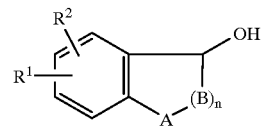

I or a pharmaceutically acceptable acid addition salt thereof; wherein n is 1,2 or 3;

A is oxygen, sulfur, $CH_2$, NH or $N(C_1-C_6)$alkyl;

B is $CR^4R^5$ wherein $R^4$ and $R^5$ are each independently selected from hydrogen, $(C_1-C_6)$alkyl, $R^6R^7(C_1-C_6)$alkyl or $R^6R^7(C_1-C_6)$alkoxy wherein $R^6$ and $R^7$ are each independently hydrogen, $(C_1-C_6)$alkyl, $(C_3-C_8)$cycloalkyl, $(C_6-C,,)$aryl or$(C_4-C,)$heteroaryl wherein the aryl and heteroaryl substituents are optionally substituted by one or two groups selected from fluoro, chloro, $(C_1-C_6)$alkyl, $(C_1-C_6)$alkoxy, perfluoro$(C_1-C_6)$alkyl, perfluoro$(C_1-C_6)$alkoxy, $(C_1-C_6)$alkylthio, $(C_1-C_6)$alkylsulfinyl, $(C_6-C_{10})$arylsulfinyl, $((C_1-C_6))$alkylsulfonyl, $(C_6-C_{10})$arylsulfonyl or $R^{14}$ $(C_8-Clo)$aryl wherein $R^{14}$ is fluoro, chloro, $(C,- C,)$alkyl, $(C_1-C_6)$alkoxy, perfluoro$(C_1-C_6)$alkyl, pernluoro$(C_1-C_6)$alkoxy, $(C_1-C_6)$alkylthio, $(C_1-C,$alkylsulfinyl or $(C_1-C_6)$alkylsulfonyl;

or $R^4$ and $R^5$ may be taken together with the carbon to which they are both attached to form a $(C_4-C_7)$cycloalkyl group;

$R^1$ is tetrazolyl, carboxy, carboxy$(C_2-C_6)$alkenyl optionally substituted by one or two $(C,-Cdalkyl$ groups; $(C_1-C_6)$ alkyl, $(C_3-C_7)$cycloalkyl, $(C_3-C,)$cycloalkyl$(C_1-C_6alkyl$ wherein the alkyl or cycloalkyl groups are optionally substituted by hydroxy, carboxy or tetrazolyl; or a group of the formula

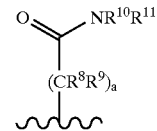

II wherein a is 0, 1, 2, 3 or 4;

$R^8$ and $R^9$ are each independently hydrogen or $(C_1-C_6$alkyl; and $R^1$ and $R^{11}$ are each independently hydrogen, hydroxy, $(C_1C_6)$alkyl, perfluoro$(C_1-C_6)$alkyl, $(C_1-C_6)$alkylsulfinyl, $(C-C_{10})$arylsulfinyl. $R^5$sulfonyl wherein $R^{15}$ is $(C_1-C_6)$ alkyl, perfluoro$(C_1-C_6,)$alkyl, $(C_3-C_8)$cycloalkyl, $(C_6-C_{10})$ aryl or $(C_4-C_9)$heteroaryl; or $(C_6-C_{10})$aryl wherein each aryl or heteroaryl substituent is optionally substituted by one or two groups selected from fluoro. chloro, $(C_1-C_6)$alkyl, $(C_1-C_6)$alkoxy, perfluoro$(C_1-C_6)$alkyl, perfluoro$(C_1-C_6)$ alkoxy, $(C_1-C_6)$alkylthio, $(C_1-C_6)$alkylsulfinyl, $(C_1-C_6)$ alkylsulfonyl and $(C_6-C_{10})$arylsulfonyl;

or a group of the formula

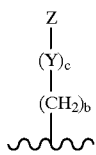
III wherein b is 0, 1, 2 or 3;

c is 0 or 1;

Y is oxygen, sulfur, CH$_2$, NH or N(C$_1$–C$_6$,)alkyl; and

Z is (C$_1$–C$_{10}$)aryl or (C$_4$–C$_9$)heteroaryl wherein the aryl or heteroaryl substituents are optionally substituted by one to three groups selected from fluoro, chloro, (C$_1$–$_6$)alkyl optionally substituted by hydroxy; R$^{12}$SO$_2$NH wherein R$^{12}$ is (C$_1$–C$_6$)alkyl or perfluoro(C$_1$–C$_6$)alkyl; R$^{13}$SO$_2$NHCO wherein R$^{13}$ is (C$_1$–C$_6$)alkyl, (C$_6$–C$_{10}$)aryl or (C$_4$–C$_9$) heteroaryl wherein aryl or heteroaryl substituents are optionally substituted by R$^{14}$ (C$_1$–C$_{10}$)aryl or R$^{14}$(C$_6$–C$_{10}$)aryl wherein R$^{14}$ is as defined above; (RSSO$_2$)NH, (RsCO)NH, (R$^5$CO$_2$)NH wherein R$^5$ is as defined above; (C$_1$–Cdalkoxy, perfluoro(C$_1$–C$_6$)alkyl, perfluoro(C$_1$–C$_6$)alkoxy, (C$_1$–C$_6$) alkylthio, (C$_1$–C$_6$)alkylsulfinyl, (C$_1$–C$_6$)alkylsulfonyl, carboxy, tetrazolyl or the group of formula 11 wherein a, R$^8$, R$^{10}$ and R$^{11}$ are as defined above; and R$^2$ is hydrogen, fluoro, chloro, (C$_1$–C$_6$)alkyl, (C$_1$–C,) alkoxy, perfluoro(C$_1$–C,)alkyl, perfluoro(C$_1$–C$_6$)alkoxy, (C$_1$–C$_6$)alkylthio, (C$_1$–C$_6$)alkylsulfinyl, (C$_6$–C$_{10}$) arylsulfinyl, (C$_1$–C$_{68}$)alkylsulfonyl or (C$_6$–C$_{10}$)arylsulfonyl.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl, optionally substituted by 1 to 3 substituents independently selected from the group consisting of fluoro, chloro, cyano, nitro, trifluoromethyl, (C$_1$–C$_6$)alkoxy, (C$_6$–C$_{10}$)aryloxy, trifluoromethoxy, difluoromethoxy and (C$_1$–C$_6$)alkyl.

The term "heteroaryl", as used herein, unless otherwise indicated, includes an organic radical derived from an aromatic heterocyclic compound by removal of one hydrogen, such as pyridyl, furyl, pyroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, optionally substituted by 1 to 2 substituents independently selected from the group consisting of fluoro, chloro, trifluoromethyl, (C$_1$–C$_6$)alkoxy, (C$_6$–C$_{10}$)aryloxy, trifluoromethoxy, difluoromethoxy and (C$_1$–C$_6$)alkyl.

The positions on the ring of formula 1, when n is 2, as used herein, are defined as follows:

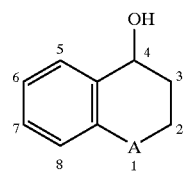
I

The compound of formula I may have chiral centers and therefore exist in different enantiomeric forms. This invention relates to all optical isomers and stereoisomers of the compounds of formula I and mixtures thereof.

A preferred embodiment of this invention relates to the above method wherein the compound administered is one wherein n is 2.

Another preferred embodiment of this invention relates to the above method wherein the compound administered is one wherein A is oxygen.

Another preferred embodiment of this invention relates to the above method wherein the compound administered is one wherein n is 2 and B, in the 3-position, is CR$^4$Rs wherein R$^1$ is hydrogen and Rs is benzyl, 4-fluorobenzyl, 4-phenylbenzyl, 4,4-fluorophenyl)benzyl or phenoxy.

Another preferred embodiment of this invention relates to the above method wherein the compound administered is one wherein R$^2$ is hydrogen or fluoro.

Another preferred embodiment of this invention relates to the above method wherein the compound administered is one wherein n is 2 and R, in the 7-position, is 2-carboxyphenyl, 2-carboxy-5chlorophenyl, 2-carboxy-4hlorophenyl, 2-carboxy-3-fluorophenyl, 2-carboxy-5-fluorophenyl, 2carboxy-5-chlorophenyl, 2carboxy-5-trifluoromethylphenyl, 2-trifluoromethylsulfonylamine-5-fluorophenyl, 2arboxy-4-fluorophenyl, 2-carboxy+fluorophenyl, 2-tetrazoyl-5-fluorophenyl or 3arboxyphenyl.

Another preferred embodiment of this invention relates to the above method wherein the compound administered is one wherein n is 2; A is oxygen; B, in the 3-position, is CR$^6$R$^1$ wherein R$^4$ is hydrogen and Rs is benzyl, 4-fluorobenzyl, 4-phenylbenzyl, 4-(4-fluorophenyl)benzyl or phenoxy; R$^2$ is hydrogen or fluoro; and R, in the 7-position, is 2arboxyphenyl, 2arboxy-5-chlorophenyl, 2carboxy-4-chlorophenyl, 2arboxy-3-fluorophenyl, 2carboxy-5-fluorophenyl, 2wrboxy-5-trifluoromethylphenyl, 2-trifluoromethylsulfonylamine-5-fluorophenyl, 2-carboxy4-fluorophenyl, 2-carboxy6-fluorophenyl, 2-tetrazoyl-5-fluorophenyl or 3arboxyphenyl.

A specific preferred embodiment of this invention relates to the above method wherein the compound administered is selected from the group consisting of:

(3S,4R)-7-(2-carboxyphenyl)-4-hydroxy-3-benzyl-2 H-1-benzopyran;

(3S,4R)-7-(2arboxy-5-chlorophenyl"-hydroxy-3-benzyl-2 H-1-benzopyran;

(3S,4R)-7-(2-carboxy4-chlorophenyl)4-hydroxy-3-benzyl-2 H-1-benzopyran;

(3S,4R)-7-(2carboxy-3-fluormphenyl)4-hydmxy-3-benzyl-2 H-1-benzopyran;

(3S,4R)-7-(2-carboxy4-fluorophenyl)4-hydroxy-3-benzyl-2 H-1-benzopyran; (3S,4R7-(2-carboxy-5-fluorophenyl)-4-hydroxy-3-benzyl-2 H-1-benzopyran;

(3S,4R)-7-(2-carboxy-5-trifluoromethylphenyl)-4-hydroxy-3-benzyl-2 H- 1 -benzopyran;

(3S,4R)-7-(2-trifluoromethylsutfonylamine-5-fluorophenyl)"ydroxy-3-benzyl-2 H-1 -benzopyran;

(3S,4R)-7, 2-tetrazoyl-5-fluorophenyl)4-hydroxy-3-benzyi-2 H-1-benzopyran; and (3S,4R)-7-(3-carboxyphenyl)-4-hydroxy-3-benzyl-2 H-1 -benzopyran.

DETAILED DESCRIPTION OF THE INVENTION

The benzopyran and benzo-fused compounds of formula I can be prepared by one or more of the synthetic methods described and referred to in U.S. Pat. No. 5,552,435 and PCT international application number PCT/IB95100397. U.S. Pat. No. 5,552,435 and PCT inte mnational application number PCT/IB95/00397 are incorporated herein by reference in their entirety.

The compounds of the invention can be administered to humans by various routes including orally, parenterally and topically, and through the use of suppositories and enemas. On oral administration, dosage levels of about 0.5 to 1000 mg/day, advantageously about 5–500 mg/day may be given in a single dose or up to three divided doses. For intravenous administration, dosage levels are about 0.1–500 mg/day, advantageously about 1.0–100 mg/day. Intravenous administration can include a continuous drip. Variations will necessarily occur depending on the age, weight and condition of the subject being treated and the particular route of administration chosen as will be known to those skilled in the art.

The compounds of the invention may be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules either alone or in admixture with excipients, or in the form of elixirs or suspensions containing flavoring or coloring agents. They can be injected parenterally, for example, intramuscularly, intravenously or subcutaneously. For parenteral administration, they are best used in the form of a sterile aqueous solution which can contain other solutes, for example, enough salt or glucose to make the solution isotonic.

Method for Heterotopic Cardiac Transplantation

Heterotopic intraabdominal cardiac transplants are performed by a modification of the method described by Corry, Transplantation, 16, 343 (1973). Allogeneic donor hearts, for example, from BlO. BR mice (H2k) are perfused retrograde with cold cardioplegia solution into the left ventricle via the aortic arch. Recipient, for example, C57BU6 mice (H2b) are prepared by ligating the lumbar vessels and isolating the abdominal aorta and vena cava. Microvascular anastomoses of donor aorta to recipient aorta and donor pulmonary artery to recipient infrarenal inferior vena cava are performed using monofilament nylon 10–0 suture. The cold ischemia time averaged is less than 25 minutes and the total duration of surgery less than 60 minutes. Transplant grafts are monitored daily by direct palpation of abdominal cardiac pulse and rated on a scale of 1 to 4. Rejection is determined as a score of 1 or less for 3 consecutive days. As a control for surgical technique and reproducibility of the murine heterotopic transplant model, syngeneic grafts, for example BIO.BR to B1O.BR or C57BV6 to C57BV6, are performed and followed for long term, indefinite survival.

The present invention is illustrated by the following examples, but it is not limited to the details thereof.

EXAMPLE 1

A. 2,4-Dihydroxy-3-chlororroriophenone

To a stirred mixture of resorcinol (200 g, 1.82 mol) and 3-chloropropionic acid (200 g, 1.84 mol) was added trifluoromethane sulfonic acid (1 kg) in one portion. The solution was heated slowly over 45 minutes to 80° C. then cooled to room temperature over 15 minutes and poured into chloroform (4.0 L). The organic portion was slowly poured into water (4.0 L) and the layers separated. The aqueous layer was extracted with chloroform (2×2.0 L). The combined organic layers were washed with brine, dried over sodium sulfate and filtered. Concentration in vacuo gave an orange semi- solid (244.1 g) which was used crude in the next step.

$^1$H-NMR (300 MHz, $CDCl_3$): 12.56 (1 H, s), 7.63 (1 H, d, J=7.6 Hz), 6.37–6.46 (2 H, m), 3.92 (2 H, t, J=6.3 Hz), 3.41 (2 H, t, J=6.3 Hz).

B. 7-Hydroxybenzorvran-4-one

To a cooled (5° C.) solution of 2N sodium hydroxide (10.0 L) was added the compound of step A (244.1 g) in one portion. The solution was warmed to room temperature over 2 hours using a warm water bath then recooled to 50C and the pH adjusted to 2 with 6M sulfuric acid (1.2 L). The mixture was extracted with 3×3.0 L of ethyl acetate, washed with brine (1×2.0 L) dried over sodium sulfate and filtered. Concentration in vacuo gave a tan solid. Trituration with hexanes, and filtration afforded 173.7 g (58% yield) of the title compound. M.P. 136° C.–137° C.

C. 7-f(Trifluoromethylsulfonyl)oxyl-benzopyran-4-one

To a stirred solution of the compound of step B (173.7 g, 1.05 mole) in methylene chloride (3.0 L) at –78° C. was added triethylamine (320 g, 3.16 mole) and dimethylaminopyridine (2.5 g). After total dissolution, trifluoromethane sulfonic anhydride (327 g, 1.16 mole) was added dropwise over 20 minutes, the material was stirred for 30 minutes at –78° C., and then warmed to room temperature over 2 hours. The reaction mixture was poured into saturated ammonium chloride solubon (2.5 L) and the layers separated. The aqueous layer was extracted with 2×2.0 L of methylene chloride. The combined organic fractions were washed with water (1×1.0 L), dried over magnesium sulfate and filtered. Concentration in vacuo gave a red oil. Chromatography over silica gel (1 kg) eluting with (8: 1) hexane: ethyl acetate gave after solvent removal 211.1 g. (69% yield) of the title product. M.P. 43–44 ° C..

D. 7-f(Trifluoromethylsulfonyl)oxyl-3-phenyimethyl-benzopyran-4-one

To a stirred solution of the product of Step C (27 g, 91.2 mmole) in 183 mL of methanol was added benzaldehyde (11.1 mL, 109 mmole) followed by pyrrolidine (9.1 mL, 109 mmole). The mixture was stirred at room temperature ovemight, cooled to 0° C. and filtered. The solid was washed once with 50 mL of ice-cold methanol and then dried in vacuo; 35.2 g, (75% yield) of the title product was recovered. M.P. 133–135° C.

$^1$H NMR (300 MHz, CDCl): 8.11 (1 H. d, J=8.7 Hz), 7.91 (1 H, bs), 7.40–7.51 (2 H, m), 7.24–7.38 (3 H, m), 6.97 (1 H, dd, J=8.7 Hz, 2.4 Hz), 6.91 (1 H, d, J=2.4 Hz), 5.40 (1 H, bs).

E. 7-[(Trifluoromethylsulfonyl)oxy]-3-phenyimethyl-benzopyran4-one

To a solution of the compound of step D (26.6 g, 69.2 mmole) in 250 mL of ethyl acetate in a 500 mL Parr shaker flask was added 10% palladium on carbon catalyst (1.3 g). The mixture was hydrogenated at 40 psi until hydrogen uptake ceased after about 3 hours. The mixture was filtered through celite (a tradename for diatamaceous earth) to remove the palladium catalyst, and chromatographed over silica gel (hexane-ether); 25.1 g (94% yield) of the title product was obtained. M.P. 56–58° C.

$^1$H NMR (300 MHz, CDCl): 8.01 (1 H, d, J=8.5 Hz), 7.20–7.35 (5 H, m), 6.981–6.96 (2 H, m), 4.42 (1 H, dd, J=11.6, 4.4 Hz), 4.22 (1 H, dd, J=11.6 Hz, 8.7 Hz), 3.26 (1 H, dd, J=14.0, 4.4 Hz), 2.90–3.05 (1 H, m), 2.70(1 H, dd, J=14.0, 8.7 Hz).

F. 7-(Trimethylstannyl)-3-phenylmethyl-benzopyran-4-one

To a stirred solution the compound of step E (9.20 g, 25.0 mmole) in 200 mL of dioxane was added lithium chloride (3.20, 75.0 mmole), Pd(PPh$_3$), (1.15 9, 1.0 mmole), 3 crystals of butylated hydroxytoluene, and hexamethylditin (9.0 g, 27.5 mmole). The mixture was heated to reflux for 1.5 hours, cooled to room temperature and poured into 150 mL of saturated, aqueous ammonium chloride solution. The mixture was extracted with 3×150 mL of diethylether and the combined organic fractions were washed with brine, dried over sodium sulfate and filtered. Evaporation in vacuo gave a yellow semi solid which was chromatographed over silica gel (5:1 hexane: ether) to give 8.90 g (89% yield) of the title product. M.P. 84–86° C.

$^1$H NMR (300 MHz,CDCl): 7.85 (1 H, d, J=8.7 Hz), 7.18–7.37 (5 H, m), 7.14 (1 H, d, J=8.7 Hz), 7.11 (1 H. s), 4.38 (1 H, dd, J=1 1.6,4.5 Hz), 4.17 (1 H, dd, J=1 1.6 Hz, 8.4 Hz), 3.28 (1 H. dd, J=14.0, 4.4 Hz), 2.84–2.95 (1 H. m), 2.71 (1 H. dd, J=114 Hz, J=1 1.0Hz), 0.31 (9 H, s).

G. 7-(3–Carbomethoxyohenyl)-3-;)henylmethyl-benzowvran-4-one

To a stirred solution of the compound of step F (7.0 g, 17.5 mmole) in dimethylformamide (DMF) (35 mL) was added Pd(PPh$_3$)$_2$Cl$_2$ (490 mg, 0.7 mmole), 3 crystals of BHT and methyl-3-iodobenzoate (5.0 g, 19.1 mmole). The mixture was stirred at reflux for 1.5 hours, cooled to room temperature and poured into 150 mL of saturated aqueous ammonium chloride solution. The mixture was extracted with 3×150 mL of diethyl ether, and the combined extract was washed with 2×1 00 mL of water, and then brine. The solution was dried over sodium sulfate, filtered and evaporated in vacuo to afford a yellow oil. Chromatography over silica gel (4:1 hexane: ether elution) afforded 6.51 g of the title compound as a viscous oil.

$^1$H NMR (300 MHz, CDClI): 8.29 (1 H, t, J=1.6 Hz), 8.06 (1 H, dd, J=7.6, 1.6 Hz), 8.00 (1 H, d, J=8.2 Hz), 7.79 (1 H, dd, J=7.6 Hz, 1.6 Hz), 7.53 (1 H, t, J=7.6 Hz), 7.22–7.36 (7 H, m), 4.41 (1 H, dd, J=11.6, 4.5 Hz), 4,21 (1 H, dd, J=11.6, 8.5 Hz), 3.94 (3 H, s), 3.31 (1 H, dd, J=14.0, 4.4hz), 2.91–2.99 (1 H, m), 2.73 (1 H, dd, J=14.0, 11.1 Hz)

H. 7-(3–Carbomethoxyphenyl)-4-hydroxy-3-phenylmethyl-benzopyran

To a stirred solution of the compound of step G (6.50 g, 17.5 mmole) in 35 mL of methanol at room temperature was added sodium borohydride (940 mg, 26.0 mmole) in one portion. The dark mixture was stirred at room temperature for 2 hours then poured into saturated aqueous ammonium chloride solution (75 mL) and extracted with 3×75 mL of diethyl ether. The combined extracts were washed with brine, dried over sodium sulfate, filtered and concentrated in vacuo to give an off-yellow oil.

Chromatography on silica gel eluting with 4:1 hexane: ether afforded first 3.26 g of the cis ring isomer of the title compound, and then 1.98 9 of the trans isomer of the title compound as viscous oils, total yield 81%.

Cis ring isomer $^1$ $^1$H NMR (300 MHz, CDCl$_3$): 8.26 (1 H, t, J=1.7 Hz), 8.02 (1 H, dt, J=7.8, 1.7 Hz), 7.76 (1 H, dt, J=7.8, 1.7 Hz), 7.50 (H, t, J=7.8 Hz), 7.41 (1 H, d, J=7.9 Hz), 7.31 (1 H, d, 7.3 Hz), 7.14–7.25 (6 H, m), 4.58 (1 H, t, J=7.2 Hz), 4.28 (1 H, dd, J=9.1, 2.5 Hz), 4.03 (1 H, dd, J=9.1, 5.4 Hz), 3.93 (3 H, s), 2.78 (1H), 2.77 (1 H, dd, J=13.7,6.2 Hz), 2.58 (1 H, dd, J=13.7,9.1 Hz),2.20–2.29 (1 H, m), 1.83 (1 H, d, J=7.2 Hz).

Trans ring isomer $^1$H NMR (300 MHz, CDCl): 8.23 (1 H, t, J=1.7 Hz), 7.98 (1 H, dt, J=7.8 Hz), 7.74 (1 H, t, J=7.8 Hz, 1.7 Hz), 7.48 (1 H, t, J=7.8 Hz), 7.20–7.36 (6 H, m), 7.15 (1 H, dd, J=8.0, 1.8 Hz), 7.09 (1 H, d, J=1.8 Hz), 4.56 (1 H, dt, J=4.7, 3.8 Hz), 4.12–4.19 (2 H, m), 3.92 (3 H, s), 2.90 (1 H, dd, J=13.6, 8.4. Hz), 2.70 (1 H, dd, J=13.6, 7.2 Hz), 2.36–2.39 (1 H, m), 1.75 (1 H, d, J=4.7 Hz).

I. N-a-t- ButoxycarbonyI-L-trvDtoDhan-7r(3-carbomethoxyohenyl)-3-ghenyimethyllchroman4-vll-ester To a stirred solution of the compound of step H (2.5 9, 6.7 mmole) in 70 ml of CH$_2$Cl$_2$ was added DMAP (897 mg., 7.34 mmole, 1.1 eq.), DCC (1.51 9, 7.34 mmole, 1.1 eq.) and N-t-Boc-L-tryptophan (2.4 9. 8.01 mmole, 1.2 eq.). The mixture was stirred at room temperature for 12 hours, filtered and washed with 1 M HCl and brine. The organic layer was dried over MgSO$_4$, filtered and concentrated in vacuo. Chromatography (silica gel-3:1 cyclohexane:ether) afforded 860 mg of the less polar diastereomer (Rf=0.3) and 700 mg of the more polar moving diastereomer (Rf--0.2). The less polar product (3S, 4R):

$^1$H-NMR (300 MHz, CDCtW; 8.29 (1 H, s), 8.03 (2 H, d, J=7.8 Hz), 7.77–7.83 (2 H, m), 7.52 (2 H, t, J=7.6 Hz), 7.02–7.33 (5 H, m), 6.64 (1 H, s), 5.65 (1 H, s), 5.06 (1 H, d, J=8.4 Hz), 4.58–4.62 (1 H, m), 3.95 (3 H. s), 3.73–3.85 (2 H, m), 3.18–3.28 (2 H, m), 2.45–2.61 (2 H, m), 2.09–2.15 (1 H, brd s), 1.39 (9 H, s). The more polar product (3R,4S);

$^1$H-NMR (300 MHz, CDCl$_3$): 8.25 (1 H, s), 8.01 (1 H. d, J=7.8 Hz), 7.94 (1 H, brd s), 7.74 (1 H, d, J=8.2 Hz), 7.54 (1 H, d, J=1 1.9 Hz), 7.48 (1 H, t, J=7.8 Hz), 7.09–7.38 (H, m), 6.95 (1 H, s), 5.61 (1 H, s), 5.08 (1 H, d, J=8.2 Hz), 4.554.60 (1 H, m), 3.94 (3 H, s), 3.73–3.76 (2 H, m), 3.22–3.35 (2 H, m), 2.42–2.60 (2 H, m), 1.90–1.96 (1 H, m), 1.39 (9 H, s).

J. 3S.4R-7-(3mrboxyphenyl)4hydroxY-3-ohenylmethyl-2 H-1 -benzopyran To a strred solution of the less polar 4R,3S tryptophan ester of step L (840 mg, 1.08 mmole) in 10 mL of methanol was added 10 mL of 2M NaOH solution. The mixture was refluxed for 8 hours, cooled and acidified to a pH of 4 with 1M HCl. The cloudy emulsion was extracted with 3×20 mL of ethyl acetate, and the combined organic fractions were washed with brine and dried over $MgSO_4$. Filtration and solvent removal in vacuo afforded a yellow foam. Chromatography (silica gel-ethyl acetate: hexane: acetic acid -35:75:1) afforded 210 mg of product.

$^1$H NMR. (300 MHz, $CD_3CN$): 8.22 (1 H, t, 1.7 Hz), 7.97 (1 H, dt, J=7.8, 1.7 Hz), 7.87 (1 H, dt, J=7.8, 1.7 Hz), 7.55 (1 H, t, J=7.8 Hz), 7.42 (1 H, d, J=7.9 Hz), 7.15–7.36 (6 H, m), 7.10 (1 H, d, J=1.8 Hz), 4.44 (1 H, d, J=4.9 Hz), 4.19 (1 H, dd, J=9.1, 2.5 Hz), 3.97 (1 H, dd, J=9.1, 5.4 Hz), 2.72 (1 H, dd, J=13.7, 6.2 Hz), 2.51 (1 H, dd, J=13.7, 9.1 Hz), 2.04–2.20 (3 H, m). [alo]=+11.1 at C=1.00 in methanol. M.P.=210–212° C.

Saponification as above of the more polar 3R,4S tryptophan-ester (700 mg) gave the 3R,4S enantiomer, $^1$H-NMR (300 MHz, $CD_3CN$): 8.22 (1 H, t, 1.7 Hz), 7.97 (1 H, dt, J=7.8, 1.7 Hz), 7.87 (1 H, dt, J=7.8, 1.7 Hz), 7.55 (1 H, t, J=7.8 Hz), 7.42 (1 H, d, J=7.9 Hz), 7.15–7.36 (6 H, m), 7.10 (1 H, d, J=1.8 Hz), 4.44 (1 H, d, J=4.9 Hz), 4.19 (1 H, dd, J=9.1, 2.5 Hz), 3.97 (1 H, dd, J=9.1, 5.4 Hz), 2.72 (1 H, dd, J=13.7, 6.2 Hz), 2.51 (1 H, dd, J=13.7, 9.1 Hz), 2.04–2.20 (3 H, m). [a],=-11.0 at c=1.01 in methanol. MP=209- 211° C.

K. Trans3-phenylmethyl-4-hydroxy-7-(3-carboxyphenyl)2 H-1 -benzopyran Saponification as in step K of the trans ring isomer of step H gave the corresponding acid.

$^1$H NMR (300 MHz, $CD_3CN$): 8.22 (1 H, t, 1.7 Hz), 7.97 (1 H, dt, J=7.8, 1.7 Hz), 7.87 (1 H, dt, J=7.8, 1.7 Hz), 7.55 (1 H, t, J=7.8 Hz), 7.42 (1 H, d, J=7.9 Hz), 7.15–7.36 (6 H, m), 7.10 (1 H, d, J=1.8 Hz), 4.44 (1 H, d, J4.9 Hz), 4.19 (1 H, dd, J=9.1, 2.5 Hz), 3.97 (1 H, dd, J=9.1, 5.4 Hz), 2.72 (1 H, dd, J=13.7, 6.2 Hz), 2.51 (1 H, dd, J=13.7, 9.1 Hz), 2.04–2.20 (3 H, m). M.P. 210–212° C.

EXAMPLE 2

The following compounds in Table 1 were prepared by saponification in accordance with Example 1J. The melting points are in degrees Celsius.

TABLE 1

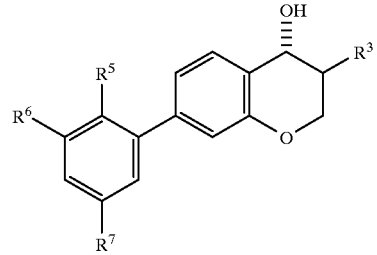

| $R^3$ | $R^5$ | $R^6$ | $R^7$ | Product |
|---|---|---|---|---|
| 4-phenylbenzyl | $CO_2H$ | H | Cl | $^1$H-NMR(300 MHz, $DMSO_{d6}$): 7.61–7.67(4H, m), 7.29–7.46 (6H, m), 6.93(1H, brd d, J=7.9Hz), 6.80(1H, br.s.), 4.38(1H, d, J=4.9Hz), 4.16 (1H, brd.d, J=11.0Hz), 4.02 (1H, dd, J=11.0, 5.6Hz), 2.96 (1H, m), 2.56(1H, m), 2.26 (1H, m). |
| benzyl | $CO_2H$ | H | $OCH_3$ | (cis)$^1$H-NMR(300MHz, $CDCl_3$): 7.96(1H, d, J=8.7Hz), 7.24–7.38(5H, m), 7.16(1H, d, J=8.0Hz), 6.88(1H, dd, J=8.7, 2.6Hz), 6.75–6.83(3H, m), 4.51(1H, d, J=2.9Hz), 4.06–4.15(2H, m), 3.84(3H, s), 2.90(1H, dd, J=13.6, 8.2Hz), 2.70(1H, dd, J=13.6, 7.2Hz), 2.27–2.39(1H, m). |
| benzyl | $CO_2H$ | H | $OCH_3$ | (trans)$^1$H-NMR(300MHz, $CDCl_3$): 7.97(1H, d, J=8.7Hz), 7.17–7.31(6H, m), 6.85(2H, dt, J=14.3, 2.8Hz), 6.81–6.85 (2H, m), 4.50(1H, d, J=4.1Hz), 4.20(1H, dd, J=11.2, 2.6Hz), 3.94(1H, dd, J=11.2, 4.8Hz), 3.86(3H, s), 2.76(1H, dd, J=13.8, 6.2Hz), 2.52(1H, dd, J=13.2, 9.4Hz), 2.22–2.30(1H, m). |
| benzyl | $CO_2H$ | H | Cl | (cis)$^1$H-NMR(300MHz, $CDCl_3$): 7.83(1H, d, J=8.4Hz), 7.16–7.38(7H, m), 7.09(1H, d, J=89.1Hz), 6.72–6.84(2H, m), 4.47(1H, d, J=2.8Hz), 4.02–4.12(2H, m), 2.85(1H, dd, J=13.6, 8.1Hz), 2.62(1H, 13.6, 7.4Hz), 2.22–2.38(1H, m). |
| benzyl | $CO_2H$ | H | Cl | (trans)$^1$H-NMR(300MHz, $CDCl_3$): 7.86(1H, d, J=8.3Hz), 7.14–7.42(8H, m), 6.76–6.84 (2H, m), 4.48(1H, d, J=4.2Hz), 4.12(1H, dd, J=11.7, 2.6Hz), 3.92(1H, dd, J=11.7, 4.4Hz), 2.73(1H, dd, J=13.7, 6.1Hz), 2.50(1H, dd, J=13.7, 9.5Hz), 2.14–2.26(1H, m). |
| benzyl | $CO_2H$ | H | H | (cis)$^1$H-NMR(300MHz, $CDCl_3$): 7.88(1H, dd, J=7.7, 1.2Hz), 7.49(1H, t, J=7.7Hz), 7.11–7.39(8H, m), 6.82–6.89 (2H, m), 4.49(1H, d, J=3.0Hz), 4.06–4.11(2H, m), 2.87(1H, dd, J=13.6, 8.0Hz), 2.63(1H, dd, J=13.6, 7.4Hz), 2.28–2.38(1H, m). |
| benzyl | $CO_2H$ | H | H | (trans)$^1$H-NMR(300MHz, $CDCl_3$): 7.88(1H, dd, J=7.7, 1.2Hz), 7.52(1H, t, J=7.7Hz), 7.10–7.41(8H, m), 6.83–6.90 (2H, m), 4.43(1H, d, |

TABLE 1-continued

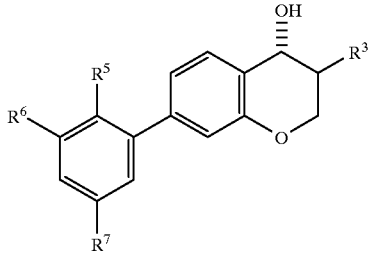

| R³ | R⁵ | R⁶ | R⁷ | Product |
|---|---|---|---|---|
| 4-phenylbenzyl | CO₂H | H | F | J=4.2Hz), 4.12(1H, dd, J=11.2, 2.9Hz), 3.88(1H, dd, J=11.2, 4.5Hz), 2.75(1H, dd, J=13.7, 5.8Hz), 2.51(1H, dd, J=13.7, 9.5Hz), 2.14–2.25(1H, m), MP 82–84° C. ¹H-NMR(300MHz, DMSO d6): 7.8(1H, dd), 7.01–7.67 (3H, m), 7.29–7.46(6H m), 6.93(HH, brd, d), 6.80(1H, d) 4.38(1H, d)4.16(1H, brd d), 4.01(1H, dd), 2.96(1H, m), 2.54(1H, m), 2.22(1H, m). |

EXAMPLE 3

By saponification of the corresponding ester in accordance with Example 1 J, 7-(4-hydroxy-3-carboxyphenyl)-4-hydroxy-3-phenylmethyl-2 H-1-benzopyran was formed having a melting point of 158–160° C. (cis) and 173–175° C. (trans).

EXAMPLE 4

A. 7-[(5-fluoro-(2-(4.4-dimethyl-2-oxazolinyl)phenyl]-3-Phenylmethylene-1 - benzopyran-4-one To a stirred solution of 2-(4-fluorophenyl)4,4-dimethyl-2- oxazoline (1.0 eq in tetrahydrofuran, .5M concentration) at –78° C. under $N_2$ was added n-butyllithium in hexanes (1.1 eq., 2.5M solution). The mixture was stirred at –78° C. for 1 hour, then $ZnCl_2$ (1M solution in ether, 1.1 eq.) was added. The mixture was warmed to 10° C. 15 over 1 hourtogive 2-(4-fluorophenyl-2-chlorozinc)-4,4-diethyl-2-oxazoline (notisolated).

To this solution was added 7-[((trifluoromethyl)sulfonyl)oxy]-3-phenylmethylene-1-benzopyran-4-one (1.0 eq.) and Pd (PPh₃)₄ (.02 eq.). The mixture was refluxed (68° C.) for 3 hours, cooled to room temperature and poured into NH₄Cl solution. The solution was extracted with 3 times diethyl ether and the combined organic fraction dried over 20 MgSO₄. Filtration followed by solvent removal in vacuo and column chromatography (silica gel—2:1 hexane:ether) gave the title compound as a yellow solid, 65% yield, m.p. 110–112° C.

¹H-NMR (300 MHz, CDCl₃): 8.04 (1 H, d), 7.91 (1 H, s), 7.78 (1 H, dd), 7.41–7.52 (3 H, m), 7.31 (2 H, d), 7.06–7.18 (3 H, m), 7.02 (1 H, s), 5.40 (2 H, s), 3.86 (2 H, s), 1.31 (6 H, s).

B. (3S*.4R*)7-[5-fluoro-(2-(4.4-dimethyl-2-oxazolinyl)phenyl]-4-hydroxy-2-phenylmethyl-2 H-1 -benzocyran To a stirred solution of the compound from step A in THF (.1M) at 0C was added LiAl H₄ (1M in ether, 2.2 eq) dropwise over 10 minutes. The mixture was warmed to room temperature and stirred for 12 hours. The mixture was cooled to oIC, quenched with Rochelles salt, and filtered through diatomaceous earth. The aqueous layer was extracted twice with ethylacetate, and the combined organic layers were washed with brine and dried over MgSO₄. Filtration an solvent removal afforded a yellow oil. Chromatography over silica gel (ethylacetate:hexane) afforded a 60% yield of a white solid. M.P. 65–700C (decomposed). Anal. calcd. for C₂₇ H2,NO₃F: C, 75.15; H. 6.07; N, 3.25. Found: C, 74.75, H, 6.02, N, 3.09.

¹H-NMR (300 MHz, CDC13) :7.70 (1 H, dd), 7.02–7.37 (8 H, m), 6.96 (1 H, dd), 7.91 (1 H, d), 4.51 (1 H, d), 4.23 (1 H, dd), 4.39 (1 H, dd) 3.87 (2 H, dd), 2.74 (1 H, dd), 2.55 (1 H, dd), 2.18–2.28 (1 H, m) 1.31 (6 H, d).

C. (3S*.4R*)7-(2carboxy-5-fluorophenyl)4-hydroxy-3-thenyimethyl-2 H-1benzopyran

The compound from step B is dissolved in methyl iodide (0.5M) at room temperature and stirred for 24 hours. The methyl iodide was removed in vacuo, the oily solid was dissolved in CH₂Cl₂ and the solvent removed in vacuo. This operation was repeated to remove traces of methyl iodide. The solid was dissolved in methanol (0.5M) and 2M NaOH (0.5M) was added. The mixture was refluxed for 5 hours, cooled to room temperature and acidified to pH 2 with 1M HCl. The mixture was extracted twice with ethyl acetate, washed with brine, and dried over MgSO₄. Filtration and solvent removal in vacuo, followed by chromatography (silica gel, 10:1 methylene chloride:methanol) gave the desired acid, 93% yield.

¹H-NMR (300 MHz, CD₃COCD3): 7.80 (1 H, dd), 7.48 (1 H, d), 7.18 (7 H, m), 7.13 (1 H, dd), 6.91 (1 H, dd), 6.80 (1 H, d), 4.52 (1 H, d), 4.23 (1 H, dd), 3.96 (1 H, dd), 2.89 (1 H, dd), 2.54 (1 H, dd), 2.19–2.30 (1 H, m).

D1. (3S.4R)-7-(2-carboxy-5-fluorophenyl)-4-hydroxy-3-phenylmethyl-2 H-1 -benzopyran The compound from step C is dissolved in diethyl ether (0.IM) and warmed to reflux. To the solution was added dropwise S(-)methylbenzylamine (1 eq) in diethyl ether (0.1 M), dropwise over 10 minutes. The mixture was cooled to room temperature and stirred for 48 hours. The precipitated salt was filtered then restirred 2 times at reflux in diethyl ether (0.1M) for 24 hours, followed by filtration. The salt (M.P.=170–173° C.) was taken up in methylene chloride and washed 3 times with 1M HCl, then once with brine, dried over MgSO₄₁ and filtered. Solvent removal in vacuo and recrystallization (1:1-hexane:ether) gave white fine crystals, more than 99.8% enantiomeric excess by HPLC analysis. [a]25=+23.8, c=0.6 in CHCl₃. M.P.=119-121° C. Anal. Calcd. for C₂₃H₁₉O₄F: c, 73.01; H. 5.06. Found: C, 72.88; H. 4.76.

D2. (3R.4S)7-(2-carboxy-5-fluorophenyl)-4-hydroxy-3-phenylmethyl-2 H-1 -benzopyran The filtrate from the combined salt slurries in step Dl was washed three times with 1M HCl, once with brine, and dried over MgSO₄. Filtration and solvent removal gave a yellow solid. A similar procedure as described in step Dl using R (+) methylbenzyl amine afforded the desired product. [a] 2=–23.4 (c=0.6 in CHCl3), M.P.=1 18–1 20° C. Anal. Calcd. for C₂₃H₁₉O₄F: C, 73.01; H. 5.06. Found: C, 73.03; H, 4.84.

EXAMPLE 5

(3S .4R)-7-(2-Trifluoromethanesulfonylamine-5-fluoroohenyl)-4-hydroxy-3-phenylmethyl-2 H-1-benzopyran A. 2,4-Dihydroxy-3chloroDroDiophenone To a stirred mixture of resorcinol (200 g, 1.82 mol) and 3-chloropropionic acid (200 g, 1.84 mol) was added trifluoromethane sulfonic acid (1 kg) in one portion. The solution was heated slowly over about 45 minutes at about 80° C. then cooled to room temperature over about 15 minutes and poured into chloroform (4.0 L). The organic portion was slowly poured into water (4.0 L) and the layers separated. The aqueous layer was extracted with chloroform (2×2.0 L). The combined organic layers were washed with brine, dried over sodium sulfate and filtered. Concentration in vacuo gave an orange semi-solid (244.1 g) which was used crude in the next step. [1]

$^1$H-NMR (300 MHz, CDCl$_3$): 12.56 (1 H, s), 7.63 (1 H, d, J=7.6 Hz), 6.37–6.46 (2 H, m), 3.92 (2 H, t, J=6.3 Hz), 3.41 (2 H, t, J=6.3 Hz).

B. 7-Hydroxybenzooyran-4-one

To a cooled (about 5° C.) solution of 2N sodium hydroxide (10.0 L) was added the compound of Example IA (244.1 g) in one portion. The solution was warmed to room temperature over about 2 hours using a warm water bath then recooled to about 5° C. and the pH adjusted to 2 with 6M sulfuric acid (1.2 L). The mixture was extracted with 3×3.0 L of ethyl acetate, washed with brine (1×2.0 L) dried over sodium sulfate and filtered. Concentration in vacuo gave a tan solid. Trituration with hexanes, and filtration afforded 173.7 g (58% yield) of the title compound of this Example I B, M.P. 136° C–137° C.

C. 7-rTrifluoromethylsulfonyloxyl-benzorvran4-one

To a stirred solution of the compound of Example 1B (173.7 g, 1.05 mole) in methylene chloride (3.0 L) at about –78° C. was added triethylamine (320 9, 3.16 mole) and dimethylaminopyridine (2.5 g). After total dissolution, trifluoromethane sulfonic anhydride (327 9,1.16 mole) was added dropwise over about 20 minutes, the material was stirred for about 30 minutes at about –78° C., and then warmed to room temperature over about 2 hours. The reaction mixture was poured into saturated ammonium chloride solution (2.5 L) and the layers separated. The aqueous layer was extracted with 2×2.0 L of methylene chloride. The combined organic fractions were washed with water (1×1.0 L), dried over magnesium sulfate and filtered. Concentration in vacuo gave a red oil. Chromatography over silica gel (1 kg) eluting with (8:1) hexane:ethyl acetate gave, after solvent removal, 211.1 g. (69% yield) of the title product. M.P. 43–44° C.

D. 7-[(trifluoromethylsulfonyl)oxy]-3-phenyl-methylene-benzopyran-4-one

To a stirred solution of the product of Example 1C (27 9, 91.2 mmole) in 183 mL of methanol was added benzaldehyde (11.1 mL, 109 mmole) followed by pyrrolidine (9.1 mL, 109 mmole). The mixture was stirred at room temperature overnight, cooled to about oeC and filtered. The solid was washed once with 50 mL of ice-cold methanol and then dried in vacuo; 35.2 9, (75% yield) of the title product of this Example 1 D was recovered. M.P. 133–135° C.

$^1$H NMR (300 MHz, CDCW: 8.11 (1 H, d, J=8.7 Hz), 7.91 (1 H, bs), 7.40–7.51 (2 H, m), 7.24–7.38 (3 H, m), 6.97 (1 H, dd, J=8.7 Hz, 2.4 Hz), 6.91 (1 H, d, J=2.4 Hz), 5.40 (11 H, bs).

E. 7-[(5-Fluoro-(2-(4.4dimethyl-2-oxazolinyl)phenyl]-1-3-phenylmethylene-1-benzopyran4-one To a stirred solution of 2-(4-fluorophenyl)-4,4-dimethyl-2-oxazoline (1.0 eq in tetrahydrofuran, 0.5M concentration) at about –78° C. under N$_2$ was added n-butyllithium in hexanes (1.1 eq., 2.5M solution). The mixture was stirred at about –78° C. for about 1 hour, then ZnCl$_2$ (1M solution in ether, 1.1 eq.) was added. The mixture was warmed to about 10IC over about 1 hour to give 2-(4-fluorophenyl-2-chlorozinc)4,4-diethyl-2-oxazoline (not isolated). To this solution was added 7[((trifluoromethyl)sulfonyl)oxy]-3-phenylmethylene-1-benzopyran-4-one (1.0 eq.) and Pd(PPh3)4 (0.02 eq.). The mixture was refluxed (about 68° C.) for about 3 hours, cooled to room temperature and poured into NH$_4$Cl solution. The solution was extracted 3 times with diethyl ether and the combined organic fraction dried over MgSO$_4$. Filtration followed by solvent removal in vacuo and column chromatography (silica gel—2:1 hexane:ether) gave the title compound of this Example IF as a yellow solid, 65% yield, m.p. 110–112° C.

$^1$H-NMR (300 MHz, CDCl$_3$): 8.04 (1 H, d), 7.91 (1 H, s), 7.78 (1 H, dd), 7.41–7.52 (3 H, m), 7.31 (2 H, d), 7.06–7.18 (3 H, m), 7.02 (1 H, s), 5.40 (2 H, s), 3.86 (2 H, s), 1.31 (6 H, s).

F. (3S*.4R*)-7–15-Fluoro-(2-(4.4-dimethyl-2-oxazolinyl)Rhenyll-4-hydroxy-3- phenylmethyl-2 H-1-benzopyran To a stirred solution of the compound from Example 1 E in THF (0.1 M) at about 0° C. was added LiAl H$_4$ (1M in ether, 2.2 eq) dropwise over about 10 minutes. The mixture was warmed to room temperature and stirred for about 12 hours. The mixture was cooled to about oeC, quenched with Rochelles salt, and filtered through diatomaceous earth. The aqueous layer was extracted twice with ethyl acetate, and the combined organic layers were washed with brine and dried over MgSO$_4$. Filtration and solvent removal afforded a yellow oil. Chromatography over silica gel (ethyl acetate:hexane) afforded a 60% yield of a white solid. M.P. 65–70° C. (decomposed). Anal. calcd. for $C_{27}$ H2e,NO$_3$F: C, 75.15; H, 6.07; N, 3.25. Found: C, 74.75, H, 6.02, N, 3.09.

$^1$H-NMR (300 MHz, CDC13): 7.70 (1 H, dd), 7.02–7.37 (8 H, m), 6.96 (1 H, dd), 7.91 (11 H, d), 4.51 (11 H, d), 4.23 (1 H, dd), 4.39 (1 H, dd), 3.87 (2 H. dd), 2.74 (11 H, dd), 2.55 (11 H, dd), 2.18–2.28 (1 H, m), 1.31 (6 H, d).

G. (3S*4R*)7-A2–Carboxy-5fluoroihenyi)-4-hydroxy-3-ghenylmethyl-2 H-benzopyran

The compound from step 1F is dissolved in methyl iodide (0.5M) at room temperature and stirred for about 24 hours. The methyl iodide was removed in vacuo, the oily solid was dissolved in CH$_2$Cl$_2$ and the solvent removed in vacuo. This operation was repeated to remove traces of methyl iodide. The solid was dissolved in methanol (0.5M) and 2M NaOH (0.5M) was added and the mixture was refluxed for about 5 hours, cooled to room temperature and acidified to pH 2 with I M HCl. The mixture was extracted twice with ethyl acetate, washed with brine, and dried over MgSO$_4$. Filtration and solvent removal in vacuo, followed by chromatography (silica gel, 10:1 methylene chloride:methanol) gave the desired acid, 93% yield.

1H-NMR (300 MHz, CD3COCDO: 7.80 (1 H, dd), 7.48 (1 H, d), 7.18 (7 H, m), 7.13 (1 H, dd) 6.91 (1 H, dd), 6.80 (1 H, d), 4.52 (1 H, d), 4.23 (1 H, dd), 3.96 (1 H, dd), 2.89 (1 H, dd), 2.54 (1 H, dd), 2.19–2.30 (1 H, m).

H1. (3S.4R)-7-(2–Carboxy-5-fluorophenyl)-4-hydroxy-3-phenyimethyl-2 H-1 - benzopyran The compound from step 1G is dissolved in diethyl ether (0.1M) and warmed to reflux. To the solution was added dropwie S(-)methylbenzylamine (1 eq) in diethyl ether (0.1M), dropwise over about 10 minutes. The mixture was cooled to room temperature and stirred for about 48 hours. The precipitated salt was filtered then stirred again at reflux in diethyl ether (0.1 M) for about 24 hours, followed by filtraton. The salt (M.P.=170–173° C.) was taken up in methylene chloride and washed 3 times with 1M HCl, then once with brine, dried over MgSO4, and filtered. Solvent removal in vacuo and recrystallization (1:1-hexane:ether) gave fine white crystals, more than 99.8% enantiomeric excess by HPLC analysis [a],25=+23.8, c=0.6 in CHC6.M.P.=1 19–121° C. Anal. Calcd. for C23 H9O4F: C, 73.01; H, 5.06. Found: C, 72.88; H, 4.76.

H2. (3R.4S)7-(2–Carboxy-5-fluorophenyl)4 hydroxy-3-phenylmethyl-2 H-1 - benzopyran The filtrate from the combined salt slurries in Example ID was washed three times with 1M HCl, once with brine, and dried over MgSO4. Filtration and solvent removal gave a yellow solid. A similar procedure as described in Example 1D using R (+) methylbenzyl amine afforded the desired product [a]D25=-23.4 (c=0.6 in CHCl3), M.P.=118–120° C. Anal. Calcd. for C23 H,O4F: C, 73.01; H, 5.06. Found: C, 73.03; H, 4.84.

I. 3S.4R)-7-(2–Carbobenzvloxyamino-5-fluoro)-4-hydroxy-3-phenylmethyl- 2 H-1-benzopyran To a solution of the compound prepared in Example 1 HI (1 mmole) in 10 mL of 1,4-dioxane was added 1.05 eq of diphenylphosphrylazide, 1.1 eq of benzyl alcohol and 2.2 eq of triethylamine. The mixture was refluxed for about 16 hours, the solvent removed under vacuum and the residue chromatographed over silica gel (1:1 -hexane: EtOAc) to afford the N-CBZ product (68% yield)

1H-NMR (300 MHz, CDCl): 8.10 (1 H, bs), 7.48–7.28 (11 H, m), 7.05 (1 H, dt, J=7.1, 2.0 Hz), 6.97–6.83 (3 H, m), 6.67 (1 H, s), 5.17 (2 H, s), 4.56 (1 H, s), 4.27 (1 H, dd, J=13.1, 1.8 Hz), 4.01 (1 H, dd, J=13.2, 5.0 Hz), 2.80 (1 H, dd, J=14.2, 7.0 Hz), 2.58 (1 H, dd, J=14.2, 9.1 Hz), 2.40–2.22 (1 H, m).

J. (3S.4R)-7-(2-Trifluoromethanesulfonylamine-5-fluoro)-4-hydroxy-3- phenylmethyl-2 H-1 -benzotvran To a solution of the compound prepared in Example 11 in 10 mL of EtOH was added 0.05 eq by weight of Pd(OH2) and the slurry was hydrogenated on a Parr shaker apparatus at 1 Atm. for about 3 hours. The mixture was filtered through Celite( and the filtrate evaporated. The yellow oil was redissolved in CH2Cl2 (10 mL), cooled to about 0° C. and triethylamine (2.2 eq) added, followed by trifluoromethanesulfonic anhydride (1.1 eq). After stirring for about 2 hours, 2 eq of solid NaOMe was added, the reaction stirred for about 15 minutes, and H2O added (10 mL). The mixture was adjusted to pH with 0.1M HCl then extracted with 3×10 mL EtOAc. The combined organic layers were washed with brine, dried over MgSO4, filtered and solvent remove under vacuum to afford a yellow semisolid. Chromatography over silica gel (1:1–10:1 EtOAc-Hexane) gave the desired sulfonamide. M.P.: 63–65° C.

What is claimed is:

1. A method for suppressing the rejection of allogeneic transplants in a mammal, including a human, comprising administering to said mammal an effective amount of a compound of the formula

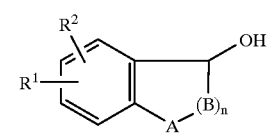

I or a pharmaceutically acceptable acid addition salt thereof; wherein n is 1, 2 or 3;

A is oxygen, sulfur, $CH_2$, NH or $N(C_1-C_6)$alkyl;

B is $CR^4R^5$ wherein $R^4$ and Rs are each independently selected from hydrogen, $(C_1-C_6)$alkyl, R6R7 $(C_1-C_6$alkyl or $R^6R^7(C -Cj$alkoxy wherein Re and $R^1$ are each independently hydrogen, $(C_1-C_6)$alkyl, $(C_3-C_9)$cycloalkyl, $(C_6-C_{10})$aryl or $(C_4-C_6)$heteroaryl wherein the aryl and heteroaryl substituents are optionally substituted by one or two groups selected from fluoro, chloro, $(C_1-C_6)$alkyl, $(C_1-C_6)$alkoxy, perfluoro $(C_1-Cj$alkyl, perfluoro$(C_1-C_6)$alkoxy, $(C_1-C_6)$alkylthio, $(C_1-CJ$alkylsulfinyl, $(C_6-C_{10})$arylsulfinyl, $(C_1-C_6)$alkylsulfonyl, $(C_6-Clo)$arylsulfonyl or $R^{14}$ $(C_8-C_{10})$aryl wherein $R^{14}$ is fluoro, chloro, $(C_1-C_6)$alkyl, $(C_1-C_6)$alkoxy, perfluoro$(C_1-C_6)$alkyl, perfluoro $(C_1-C_6)$alkoxy, $(C_1-C_6)$alkyfthio, $(C_1-C_6)$alkylsulfinyl or $(C_1-C_6)$alkylsulfonyl;

or $R^4$ and Rs may be taken together with the carbon to which they are both attached to form a $(C_4-C_7)$ cycloalkyl group;

$R^1$ is tetrazolyl, carboxy, carboxy$(C_2-Cj$alkenyl optionally substituted by one or two $(C_1-Cd$alkyl groups; $(C_1-C_6)$alkyl, $(C_3-C_7)$cycloalkyl, $(C_3-C_6)$cycloalkyl $(C_1-Cj$alkyl wherein the alkyl or cycloalkyl groups are optionally substituted by hydroxy, carboxy or tetrazolyl; or a group of the formula

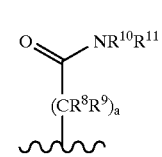

II wherein a is 0, 1, 2, 3 or 4;

$R^8$ and $R^5$ are each independently hydrogen or $(C_1-C_6)$ alkyl; and $R^{10}$ and $R^{"1}$ are each independently hydrogen, hydroxy, $(C_1-C_6)$alkyl, perfluoro$(C_1-C_6)$alkyl, $(C_1-CO)$ alkylsutfinyl, $(C_6-C_{10})$aryisulfinyl, $R^{15}$sulfonyl wherein $Rl^5$ is $(C_1-C_6)$alkyl, perfluoro$(C_1-C_6)$alkyl, $(C_3-C_8)$cycloalkyl, $(C_6-Clo)$aryl or $(C_4-C_9)$heteroaryi;

or $(C_6-C_{10})$aryl wherein each aryl or heteroaryl substituent is optionally substituted by one or two groups selected from fluoro, chloro, $(C_1-C_6)$alkyl, $(C_1-C_6)$alkoxy, perfluoro$(C_1-C_6)$alkyl, perfluoro$(C_1-C_6)$alkoxy, $(C_1-C_6)$alkylthio, $(C_1-C_6)$alkylsulfinyl, $(C_1-C_6)$alkylsulfonyl and $(C_6-C_{10})$arylsulfonyl;

or a group of the formula

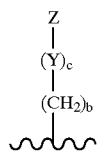

III wherein b is 0, 1, 2 or 3;

c is 0 or 1;

Y is oxygen, sulfur, $CH_2$, NH or $N(C_1-C_6)$alkyl; and

Z is $(C_6-C_{10})$aryl or $(C_4-C_9)$heteroaryl wherein the aryl or heteroaryl substituents are optionally substituted by one to three groups selected from fluoro, chloro, $(C_1-C_6)$alkyl optionally substituted by hydroxy; $R^{12}SO_2NH$ wherein $R^{12}$ is $(C_1-C_6)$alkyl or perfluoro $(C_1-C_6)$alkyl; $R^{13}SO_2NHCO$ wherein $R^{13}$ is $(C_1-CO)$alkyl, $(C_6-C_{10})$aryl or $(C_4-C9)$heteroaryl wherein aryl or heteroaryl substituents are optionally substituted by $R^{14}$, $(C_6-C_{10})$aryl or $R^{14}(C_6-C_{10})$aryl wherein $R^{14}$ is as defined above; $(R"^5SO_2)NH$, $(R5CO)NH$, $(R" CO_2)$NH wherein $R^{15}$ is as defined above; $(C_1-C_6)$alkoxy, perfluoro$(C_1-C_6)$alkyl, perfluoro$(C_1-C_6)$alkoxy, $(C_1-C_6)$alkylthio, $(C_1-C_8)$alkylsutfinyl, $(C_1-C_6)$alkylsulfonyl, carboxy, tetrazolyl or the group of formula 11 wherein a, RI, $R^9$, $R°$ and $R^{11}$ are as defined above; and $R^2$ is hydrogen, fluoro, chloro, $(C_1-C_6)$alkyl, $(C_1-C_6)$alkoxy, perfluoro$(C-C_6)$alkyl, perfluoro$(C_1-C_6)$alkoxy, $(C_1-C_6)$alkythio, $(C_1-C_6)$alkylsuffinyl, $(C_6-Clo)$arylsuffinyl, $(C_1-C_6)$alkylsuffonyl or $(C_6-C_{10})$arylsulfonyl.

2. A method according to claim 1, wherein the compound that is administered Is one wherein n is 2.

3. A method according to claim 1, wherein the compound that is administered is one wherein A Is oxygen.

4. A method according to claim 1, wherein the compound that Is administered is one wherein n is 2 and B, in the 3-position, is $CR^4R^5$ wherein $R^1$ is hydrogen and $R^5$ is benzyl, 4-fluorobenzyl, 4-phenylbenzyl, 4-(4-fluorophenyl)benzyl or phenoxy.

5. A method according to claim 1, wherein the compound that Is administered is one wherein $R^2$ is hydrogen or fluoro.

6. A method according to claim 1, wherein the compound that is administered is one wherein n is 2 and RI, in the 7-position, is 2rboxyphenyl, 2- carboxylhlorophenyl, 2-carboxychlorophenyl, 2carboxyfiuorophenyl, 2-carboxy-5-fluorophenyl, 2-carboxy-5-chlorophenyl, 2rboxy-trifluoromethylphenyl, 2-trifluoromethylsulfonylaminefluorophenyl, 2rboxy4fluorophenyl, 2rboxyS fluorophenyl, 2-tetrazoyl-5-fluorophenyl or 3-carboxyphenyl.

7. A method according to claim 1, wherein the compound that is administered is one wherein n is 2; A is oxygen; B, in the 3-position, is $CR^4FR$ wherein R4 is hydrogen and Rs is benzyl, 4-fluorobenzyl, 4-phenylbenzyl, 4-(4-fluorophenyl)benzyl or phenoxy; $R^2$ is hydrogen or fluoro; and RI, in the 7-position, is 2 carboxyphenyl, 2caboxy-5chlorophenyl, 2wboxychlorophenyl, 2rboxyf fluorophenyl, 2-carboxy-5-fluorophenyl, 2-carboxy-5-trifluoromethylphenyl, 2- trlfluoromethylsuifonylamine-5-fluorophenyl, 2rboxy4fluorophenyl, 2rboxy6 fluorophenyl, 2-tetmzoyifiuorophenyl or 3rboxyphenyl.

8. A method according to claim 1, wherein said compound is selected from the group consisting of:

(3S,4R)-7-(2rboxyphenyl)hydroxy3benzyl-2 H-1 benzopyran;

(3S,4R)-7-(2-carboxyschlorophenyl)hydroxyffibenzyi-2 H-1 -benzopyran;

(3S,4R)-7-(2carboxychlorophenyl)hydroxyfbenzyl-2 H-1 -benzopyran;

(3S,4R)-7-(2rboxy-fluorophenyl)4hydroxybenzyl-2 H-1 -benzopyran;

(3S,4R)-7-(2-carboxy44fluorophenyl)4hydroxy4benzyl-2 H-1 -benzopyran; (3S,4R)-7-(2rboxyuorophenyl) 4ydroxyfbenzyl-2 H-1-benzopyran;

(3S ,4R)-7-(2-carboxy-5-trifluoromethylphonyl)-4-hydroxy-3-benzyl-2 H-1 - benzopyran;

(3S,4R7q2-tffluoromethylsufonylamine5fluorophonyl)+hydroxyfbenzyl-2 H- 1 -benzopyran;

(3S,4R)-7-(2tetrazoyfluorophenyl) 4ydroxyenzyl-2 H-1-benzopyraniand (3S,4R)-7-(3-carboxyphenyl) 4hydroxyfbenzyl-2 H-1 -benzopyran.

* * * * *